United States Patent [19]

Nakajima

[11] Patent Number: 4,873,985
[45] Date of Patent: Oct. 17, 1989

[54] ULTRASONIC IMAGING APPARATUS UTILIZING DOPPLER FLOW METERING

[75] Inventor: Hirotaka Nakajima, Tochigi, Japan

[73] Assignee: Kabushiki Kaisha Toshiba, Kawasaki, Japan

[21] Appl. No.: 140,680

[22] Filed: Jan. 4, 1988

[30] Foreign Application Priority Data

Jan. 12, 1987 [JP] Japan ................................. 62-3204

[51] Int. Cl.⁴ .............................................. A61B 8/06
[52] U.S. Cl. ............................ 128/661.09; 128/661.1; 128/660.05
[58] Field of Search ..................... 128/660, 663, 661.1, 128/661.09, 660.05, 916; 73/861.25, 625, 628, 633

[56] References Cited

U.S. PATENT DOCUMENTS

| | | |
|---|---|---|
| 4,062,237 | 12/1977 | Fox ................................. 128/660.05 |
| 4,257,278 | 3/1981 | Papadofrangakis et al. ....... 128/663 |
| 4,373,533 | 2/1983 | Iinuma ............................ 128/660.05 |
| 4,501,277 | 2/1985 | Hongo ................................. 128/663 |
| 4,530,363 | 7/1985 | Brisken ................................ 128/663 |
| 4,570,488 | 2/1986 | Miwa et al. .................... 128/661.01 |
| 4,640,291 | 2/1987 | 't Hoen ................................ 128/660 |

Primary Examiner—Francis Jaworski
Attorney, Agent, or Firm—Finnegan, Henderson, Farabow, Garrett & Dunner

[57] ABSTRACT

An ultrasonic imaging apparatus includes an ultrasonic transducer having a matrix of a plurality of ultrasonic transducer elements, and a transmitter/receiver circuit for driving the ultrasonic transducer elements with delay control so that the ultrasonic transducer selectively generates ultrasonic beams in X and Y scanning directions. A marker is set in a tomographic image obtained by scanning a subject in the X direction. The subject is scanned in the Y direction along the marker. A section image corresponding to the marker is output.

9 Claims, 4 Drawing Sheets

ULTRASONIC IMAGING APPARATUS UTILIZING DOPPLER FLOW METERING

BACKGROUND OF THE INVENTION

The present invention relates to an ultrasonic imaging apparatus and, more particularly, to an ultrasonic imaging apparatus capable of measuring the amount of a fluid flowing in an object under examination.

An electronic scanning type ultrasonic transducer comprises an array of a plurality of ultrasonic transducer elements. When a subject having a blood vessel is scanned by the ultrasonic transducer, Doppler information and section-area information of the blood vessel can be obtained. The amount of blood flow in the subject is measured from this information.

When the amount of blood flow is to be measured using a conventional one-dimensional array type ultrasonic transducer, first, the ultrasonic transducer scans a longitudinal section-area of a blood vessel in order to obtain a Doppler signal, and then a cross-section of the blood vessel to obtain the sectional area of the blood vessel. When the scanning direction is to be switched from the longitudinal direction to the cross-section, it is required to change the location of the ultrasonic transducer. In this case, the positions where the Doppler signal and the section-area information are obtained are undesirably displaced, and an error occurs in the amount of blood flow obtained from the Doppler information and the section-area information.

SUMMARY OF THE INVENTION

It is an object of the present invention to provide an ultrasonic imaging apparatus which can correctly measure an amount of blood flow without accompanying a positional displacement between the positions where Doppler information and section-area information are obtained.

According to the present invention, there is provided an ultrasonic imaging apparatus comprising an ultrasonic transducer having a matrix of a plurality of ultrasonic transducer elements, and means for driving the ultrasonic transducer elements with delayed drive signals so as to selectively output ultrasonic beams in a first scanning direction and a second scanning direction perpendicular to it.

When the matrix type ultrasonic transducer scans a subject in the first scanning direction with the ultrasonic beam, it outputs an image signal in the longitudinal section of a blood vessel, and a Doppler signal is obtained from the image signal. When the scanning direction is switched to the second scanning direction, the image obtained by scanning the subject in the second scanning direction indicates a section of the blood vessel. An amount of blood flow in the blood vessel is measured from the section-area of the blood vessel and the Doppler information.

DETAILED EXPLANATION OF THE PREFERRED EMBODIMENT

Figure 1:
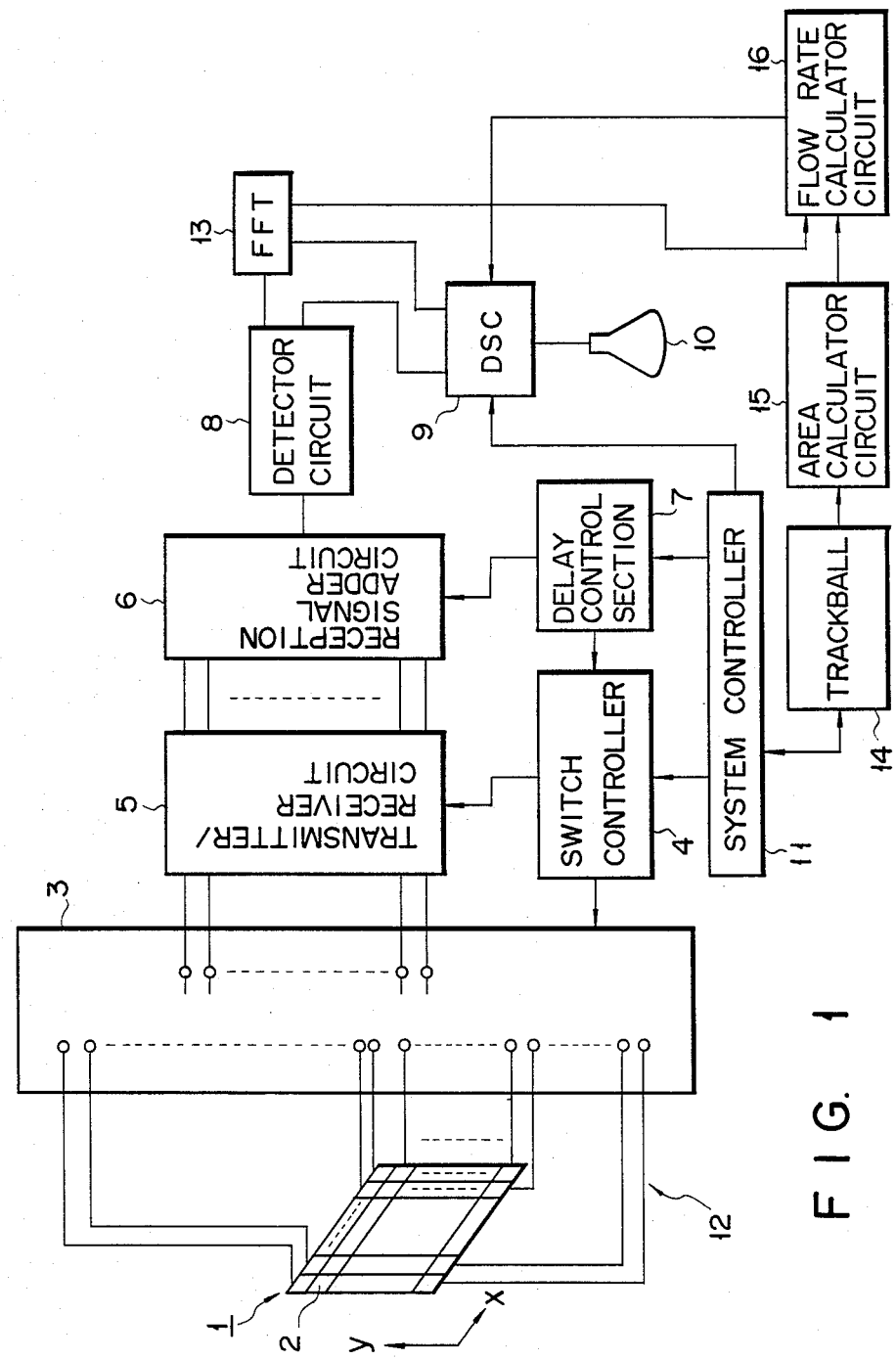
FIG. 1 is a block diagram of an ultrasonic imaging apparatus according to an embodiment of the present invention.
Figure 3:
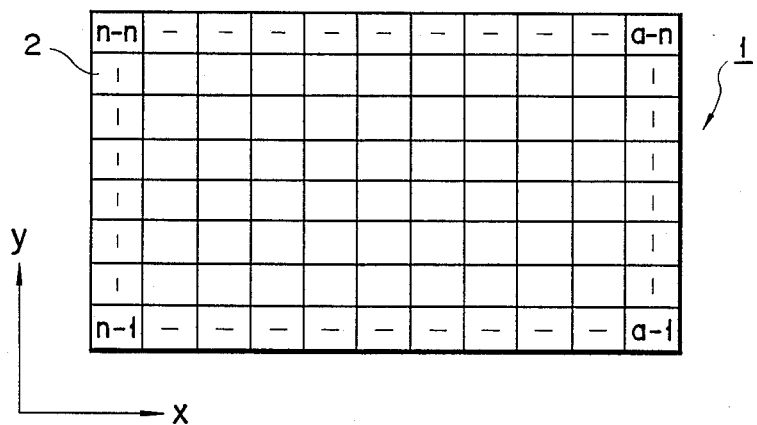
FIG. 3 is a plan view of a matrix type ultrasonic transducer used in the ultrasonic imaging apparatus of the present invention.

Referring to the apparatus shown in FIG. 1, ultrasonic transducer 1 comprises a matrix of a plurality of ultrasonic transducer elements ($64 \times 64$ elements) n-1 -n-n to a-1 - a-n, as shown in FIG. 3. The ultrasonic transducer elements are connected to a plurality of contacts of switch circuit 3. A plurality of switching contacts of switch circuit 3 are connected to transmitter/receiver circuit 5. Switch circuit 3 is switched by the control of switch control section 4.

Transmitter/receiver circuit 5 is of a type generally used in an ultrasonic transducer and comprises a drive pulse generator, a delay circuit, a receiver delay circuit, and the like. The output terminals of the receiver of transmitter/receiver circuit 5 are connected to reception signal adder circuit 6. Transmitter/receiver section 5 and reception signal adder circuit 6 are connected to delay control section 7 (to be described later) for controlling the delay times of their delay circuits.

The output terminal of reception signal adder circuit 6 is connected to detector circuit 8. When Doppler information is to be obtained, an output signal from adder circuit 6 is subjected to orthogonal detection by detector circuit 8. When B mode information is to be obtained, the output signal is subjected to amplitude detection by detector circuit 8.

The Doppler output terminal of detector circuit 8 is connected to an input terminal of FFT (Fast Fourier Transformer) 13. FFT 13 subjects a detection signal obtained by detector circuit 8 to fast Fourier transformation in order to analyze the waveform of the detection signal.

The output terminals of detector circuit 8 and FFT 13 are connected to digital scan converter (DSC) 9. DSC 9 converts a B mode signal and a Doppler signal output from detector circuit 8 and FFT 13, respectively, into image signals, and includes a plurality of frame memories. The output terminal of DSC 9 is connected to CRT display 10.

System controller 11 is provided to control the entire apparatus of the present invention and is mainly constituted by a CPU. Referring to FIG. 1, controller 11 is connected to switch control section 4, delay control section 7, and DSC 9, and controls them. System controller 11 is also connected to trackball 14. Trackball 14 is used to set a marker or the like on an image displayed on CRT display 10 through system controller 11 and DSC 9.

Trackball 14 is connected to area calculator circuit 15 for calculating the cross-sectional area of a blood vessel as will be described later. The output terminal of calculator circuit 15 is connected to flow rate calculator circuit 16. Flow rate calculator circuit 16 calculates an amount of blood flow in a blood vessel from the cross-sectional area calculated by area calculator circuit 15 and Doppler information, i.e., flow rate information obtained by FFT 13. Since the output terminal of flow rate calculator circuit 16 is coupled to DSC 9, the calculated amount can be displayed on CRT display 10.

Figure 2:
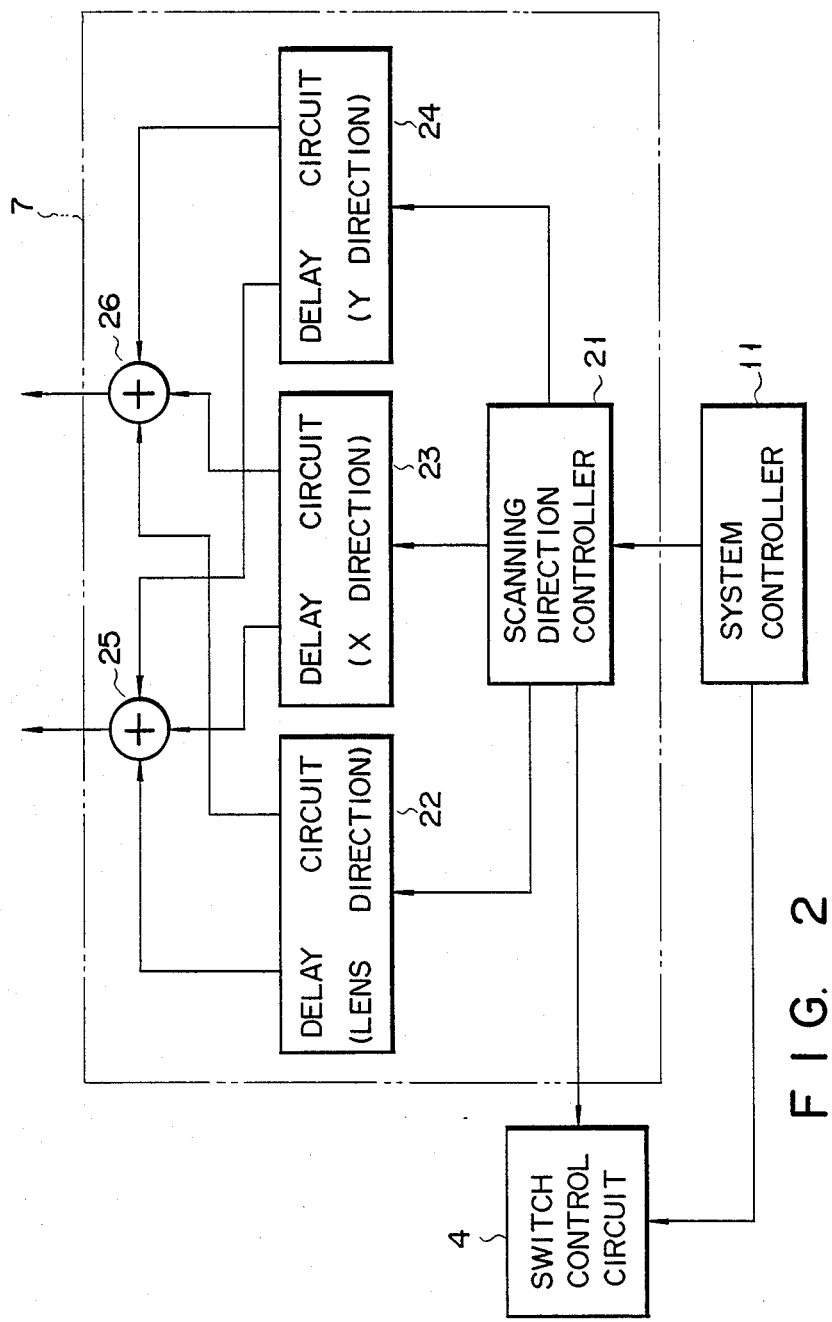
FIG. 2 is a block diagram of a delay control section shown in FIG. 1.
Figure 6:
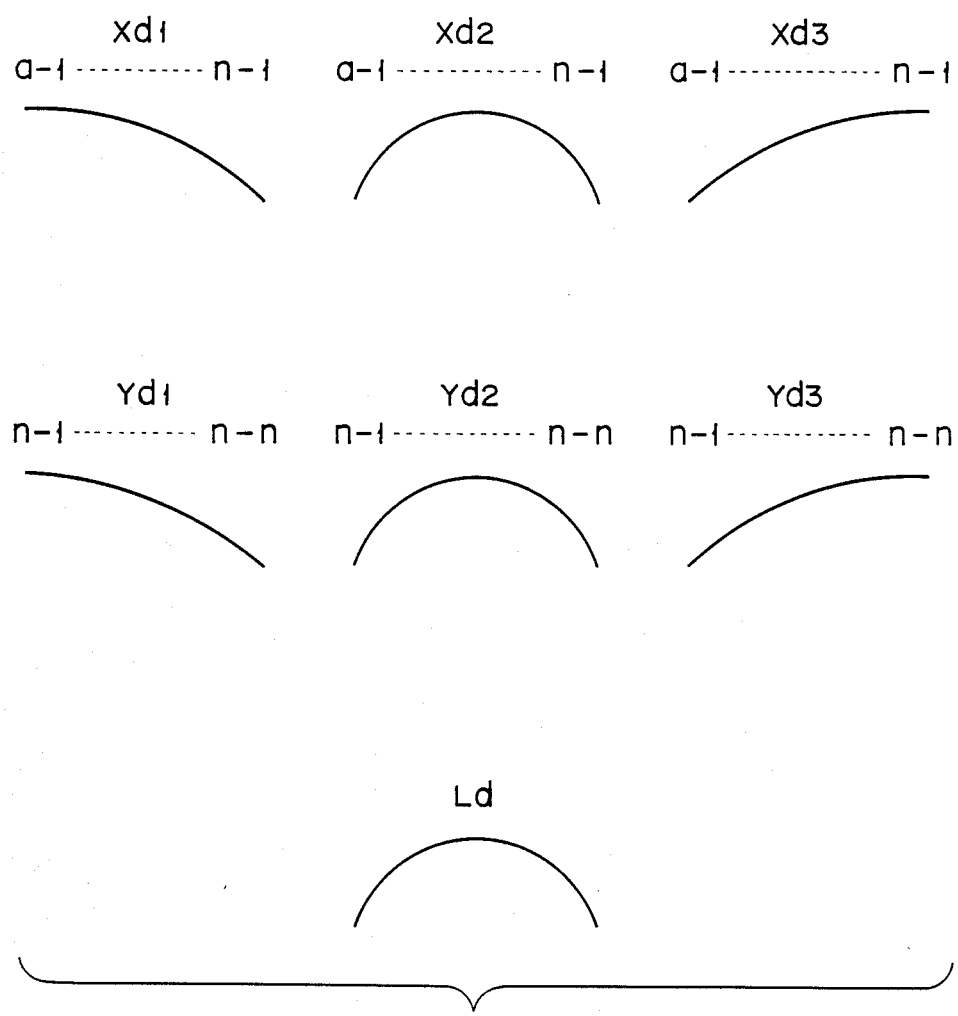
FIG. 6 shows delay curves of a drive signal that drives the matrix type transducer.

Delay control section 7 has an arrangement as shown in FIG. 2. More specifically, the output terminals of scanning direction controller 21 are connected to lens direction delay circuit 22, X direction delay circuit 23, and Y direction delay circuit 24. Controller 21 is controlled by system controller 11 and outputs delay control signals to delay circuits 22, 23, and 24 in accordance with the scanning direction. Delay circuits 22, 23, and 24 output a delay signal having a delay characteristic as shown in FIG. 6.

The operation of the ultrasonic imaging apparatus having the above circuit arrangement will be described.

When the subject is scanned in an X-direction, the following delay times are determined for ultrasonic transducer elements n-1 to a-c of ultrasonic transducer 1. More specifically, X direction delay amounts Xd1, Xd2, and Xd3, for example, as shown in FIG. 6, are determined according to the scanning direction of the ultrasonic beam in the X direction. Fixed lens direction delay amount Ld is determined for focusing the ultrasonic beam in the Y direction. A Y direction delay amount is set to determine the direction of the beam depending on the cross-sectional direction of the subject. For example, when a tomographic image perpendicular to the surface of transducer 1 is to be obtained, fixed Y direction delay amount Yd2 is set in delay circuit 24. Therefore, in order to scan the subject in the X-direction, a delay amount obtained by synthesizing X direction delay amounts Xd1, Xd2, and Xd3, lens direction delay amount Ld, and Y direction delay amount Yd2 is supplied to ultrasonic transducer elements n-1 to a-n.

When delay amounts are set in delay circuits 22 to 24 by scanning direction controller 21, switch controller 4 switches switch circuit 3 by a control signal supplied from system controller 11 in order to supply set delay amounts to corresponding ultrasonic transducer elements. As a result, drive pulses output from transmitter/receiver circuit 5 with set delay amounts are applied to corresponding ultrasonic transducer elements through switch circuit 3, and ultrasonic transducer 1 emits an ultrasonic beam for sector-scanning the subject in the X direction.

An echo wave reflected from the subject is converted into echo signals by ultrasonic transducer 1, and the echo signals are input to transmitter/receiver circuit 5 through switch circuit 3. The echo signals are amplified by transmitter/receiver circuit 5 and input to reception signal adder circuit 6 so that they are added to the content of adder circuit 6. Before this addition, the echo signals are delayed by a delay signal supplied from delay control section 7.

Figure 4:
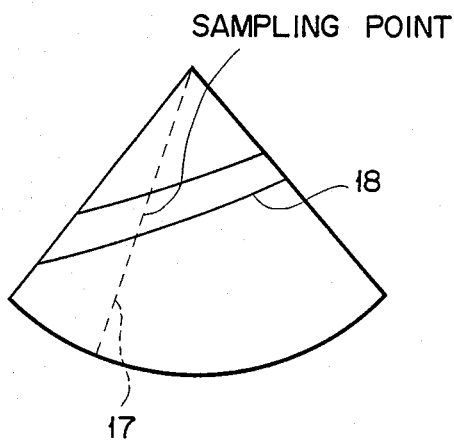
FIG. 4 shows an image obtained by ultrasonic scanning of a longitudinal section of a blood vessel.

An output signal from adder circuit 6 is subjected to amplitude detection by detector circuit 8 and input to DSC 9. DSC 9 converts an amplitude detection signal into an image signal, and stores the image signal in, e.g., a 1st frame memory included in DSC 9. When an image signal read out from the 1st frame memory is input to CRT display 10, CRT 10 displays the input image signal as, e.g., a tomographic image (B mode image) including a longitudinal section of blood vessel 18, as shown in FIG. 4.

The operator observes the image displayed on CRT display 10. Upon operation of trackball 14 by the operator, system controller 11 inputs marker information in DSC 9 in accordance with the shift of trackball 14. As a result, the marker information is displayed as marker 17 superposed on the display image on CRT display 10.

When marker 17 has located a sampling position crossing blood vessel image 18 by the operation of trackball 14, a Y scanning delay amount is set in delay control section 7. In this case, the delay amounts supplied to the X-direction ultrasonic transducer elements are determined in accordance with delay amount Ld for focusing the ultrasonic beam in the X direction, and a delay amount for determining a sectional direction along the X direction, i.e., the direction of marker 17, e.g., a delay amount between Xd1 and Xd2. Y scanning delay amounts Ya1, Ya2, and Ya3 shown in FIG. 6 are sequentially supplied to the Y-scanning ultrasonic transducer elements.

When the Y direction scanning delay amounts are set as described above, switch controller 4 switches switch circuit 3 by a control signal supplied from system controller 11 so that the set delay amounts are supplied to the corresponding ultrasonic transducer elements. Then, drive pulses output from transmitter/receiver circuit 5 with set delay amounts are applied to the corresponding ultrasonic transducer elements through switch circuit 3, and ultrasonic transducer 1 emits an ultrasonic beam for sector-scanning the subject in the Y direction.

The echo wave reflected by the subject is converted into echo signals by ultrasonic transducer 1, and the echo signals are input to transmitter/receiver circuit 5 through switch circuit 3. The echo signals are amplified by transmitter/receiver circuit 5 and input to reception signal adder circuit 6 to be added with the content of adder circuit 6. Before the addition, the echo signals are delayed by the delay signal output from delay control section 7.

Figure 5:
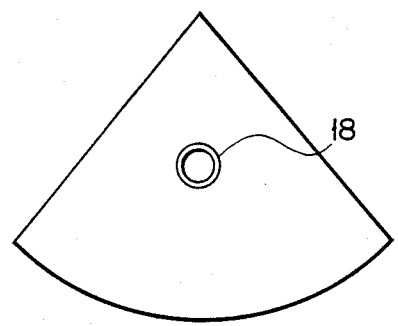
FIG. 5 shows an image obtained by ultrasonic scanning of a cross-section of the blood vessel.

An output signal from adder circuit 6 is subjected to amplitude detection by detector circuit 8 and input to DSC 9. DSC 9 converts an amplitude detection signal into an image signal and stores the image signal in, e.g., its 2nd frame memory. Upon reception of an image signal read out from the 2nd frame memory, CRT display 10 displays it as a tomographic image (B mode image) including a cross-section of blood vessel 18, as shown in FIG. 5. When the image signals of the 1st and 2nd frame memories of DSC 9 are read out simultaneously and input to CRT display 10, the images shown in FIGS. 4 and 5 can be displayed on different display areas of CRT display 10 simultaneously.

In this embodiment, X and Y direction delay amounts are separately provided. However, a single delay amount may be sufficient if the scanning angles are the same in both X and Y direction scannings.

Referring to FIG. 4, an echo signal of blood vessel 18 obtained along marker 17 is subjected to orthogonal detection by detector circuit 8 and converted into a Doppler signal. The Doppler signal is processed by FFT 13 and input to flow rate calculator circuit 16. Calculator circuit 16 calculates an amount of blood flow from the cross-section information of the blood vessel obtained by area calculator circuit 15 and the Doppler information. When the calculated amount information is input to CRT display 10 through DSC 9, it is displayed on it.

When the sectional area of blood vessel 18 is to be calculated, the operator sets a cross-section measuring marker in blood vessel 18 shown in FIG. 5 using trackball 14. The sectional area of the blood vessel is calculated by area calculator circuit 15 from the set information, e.g., blood vessel diameter information.

When the sectional area of the blood vessel is to be calculated, the maximum diameter of blood vessel 18 is obtained based on the B mode image shown in FIG. 5, and the sectional area can be automatically calculated from the obtained diameter. In this case, the sectional area is calculated by the CPU based on the B mode image signal stored in the frame memories. For example, the sectional area is obtained from the number of pixels corresponding to the blood vessel diameter.

In this embodiment, B mode information for two orthogonal cross-sections is obtained. However, the intersecting angle of the two B mode images can be arbitrarily executed by adjusting the X and Y direction delay amounts. The X or Y direction ultrasonic transducer elements are divided into a plurality of groups, and a plurality of tomographic images can be obtained when the respective groups scan different portions of the object. Furthermore, the apparatus according to the present invention can be used not only for measuring the amount of blood flow upon sampling, but also to find a constriction of a blood vessel when two orthogonal sections of an object are observed simultaneously.

As described above, in the present invention, a matrix type ultrasonic transducer is used, and the scanning direction of the ultrasonic beam is electronically switched in order to obtain tomographic images of orthogonal directions. As a result, a measurement error caused by positional displacement of orthogonal section images is eliminated in measurement of the amount of blood flow.

What is claim is:

1. An ultrasonic imaging apparatus comprising:
   ultrasonic transducer means, having a plurality of ultrasonic transducer elements arranged in a matrix having column and row lines, for emitting first and second ultrasonic beams to an object having a blood vessel extending in a predetermined direction therein and for converting echoes of the ultrasonic beams into first and second echo signals;
   driving means, coupled to said ultrasonic transducer means, for selectively driving said transducer elements for generating the first ultrasonic beam for scanning the object in a first B-scan orientation corresponding to the row lines, to obtain a first B-mode image, and the second ultrasonic beam for scanning the object in a second B-scan orientation corresponding to the column lines, to obtain a second B-mode image crossing the first B-mode image;
   means for designating a selected scanning position in the second B-scan orientation, the second B-mode image crossing the first B-mode image at the selected scanning position;
   means for converting, into first and second image signals corresponding to the first and second B-mode images, respectively, the first and second echo signals output from said ultrasonic transducer means, said first and second echo signals corresponding to the echo signals obtained by scanning the object in the first and second B-scan orientations, said converting means including means for detecting a Doppler component from the first image signal; and
   display means, coupled to said transducer means, responsive to the first and second image signals for displaying the first and second B-mode images.

2. An apparatus according to claim 1, wherein said driving means includes means for outputting, to said ultrasonic transducer means, first and second drive signals, said ultrasonic transducer means being driven by the first drive signal to generate the first ultrasonic beam in the first B-scan orientation along the extending direction of the blood vessel and said ultrasonic transducer means being driven by the second drive signal to generate the second ultrasonic beam for scanning the blood vessel in the second B-scan orientation perpendicular to the extending direction of the blood vessel.

3. An apparatus according to claim 4, wherein said Doppler component detecting means comprises means for detecting a signal component corresponding to blood flowing through the blood vessel from the first image signal corresponding to the first B-scan orientation, and means for processing the signal component to obtain orthogonal conversion information.

4. An apparatus according to claim 1, wherein said designating means includes means for outputting, to said drive means, a marker signal indicating the selected scanning position in the second B-scan orientation, said marker signal being displayed as a line marker on said display means, said line marker crossing a desired position on the B-mode image corresponding to the first image signal, the desired position corresponding to the selected scanning position.

5. An apparatus according to claim 4, wherein said driving means drives said ultrasonic transducer means to generate the second ultrasonic beam for scanning the object in the second B-scan orientation, along the line marker displayed on said display means.

6. An apparatus according to claim 1, wherein said driving means includes delay means for providing a first delay amount, suitable for scanning the object in the first B-scan orientation and a second delay amount, suitable for focusing the ultrasonic beam.

7. An apparatus according to claim 1, wherein said driving means includes means for generating a drive pulse to drive said ultrasonic transducer means, and switching circuit means, connected between said ultrasonic transducer means and said drive pulse generating means, for selectively guiding the drive pulse to said ultrasonic transducer elements.

8. An apparatus according to claim 1, wherein said signal converting means includes means for storing the first and second image signals, and said display means includes a plurality of different display areas for respectively displaying image signals read out from said memory means.

9. An ultrasonic imaging apparatus comprising:
   ultrasonic transducer means, having a plurality of ultrasonic transducer elements arranged in a matrix having row and column lines, for emitting first and second ultrasonic beams to an object and for converting echoes of the ultrasonic beams into first and second echo signals;
   driving means, coupled to said ultrasonic transducer means, for driving said transducer elements for generating the first ultrasonic beam for scanning the object in a first B-scan orientation corresponding to the row lines, to obtain a first B-mode image;
   means for converting, into a first image signal, the echo signal output from said ultrasonic transducer means and corresponding to the first ultrasonic beam, said converting means including means for detecting a Doppler component from the first image signal;
   display means, coupled to said transducer means, for displaying the first image signal as the first B-mode image; and means for designating, on the first B-mode image, a selected scanning position in a second B-scan orientation corresponding to the column lines;

wherein said driving means drives said transducer elements for generating a second ultrasonic beam for scanning the object in the second B-scan orientation, to obtain a second B-mode image crossing the first B-mode image at the selected scanning position;

said converting means converts, into a second image signal, an echo signal output from said ultrasonic transducer means and corresponding to the second ultrasonic beam; and said display means displays the second image signal as the second B-mode image corresponding to a tomogram of the object along the second B-scan orientation.

* * * * *

UNITED STATES PATENT AND TRADEMARK OFFICE
CERTIFICATE OF CORRECTION

PATENT NO. : 4,873,985
DATED : October 17, 1989
INVENTOR(S) : Hirotaka Nakajima

It is certified that error appears in the above-identified patent and that said Letters Patent is hereby corrected as shown below:

Claim 3, Column 6, Line 10, "claim 4" should be
--claim 2--.

Signed and Sealed this

Thirteenth Day of October, 1992

Attest:

DOUGLAS B. COMER

Attesting Officer     Acting Commissioner of Patents and Trademarks